US005482049A

United States Patent [19]
Addiss et al.

[11] Patent Number: 5,482,049
[45] Date of Patent: Jan. 9, 1996

[54] PROGRAMMABLE ELECTRONIC BLOOD PRESSURE MONITORING LABELS

[75] Inventors: Robert R. Addiss, Bedford; Stephen E. Gordon, Cambridge; Stephen J. Staats, Wenham, all of Mass.

[73] Assignee: Siemens Medical Systems, Inc., Iselin, N.J.

[21] Appl. No.: 214,345

[22] Filed: Mar. 16, 1994

[51] Int. Cl.⁶ ........................................ A61B 5/00
[52] U.S. Cl. .................. 128/673; 128/672; 128/675; 128/903
[58] Field of Search .................... 128/903, 904, 128/668, 672, 673, 675, 677–683, 687

[56] References Cited

U.S. PATENT DOCUMENTS

| | | | |
|---|---|---|---|
| 3,831,006 | 8/1974 | Chaffin, III et al. | 235/61.7 |
| 4,189,936 | 2/1980 | Ellis | 73/4 R |
| 4,215,879 | 8/1980 | Blum | 283/21 |
| 4,264,979 | 4/1981 | Gutowski | 455/77 |
| 4,319,241 | 3/1982 | Mount | 128/904 |
| 4,944,305 | 7/1990 | Takatsu et al. | 128/680 |
| 5,101,828 | 4/1992 | Welkowitz et al. | 128/668 |
| 5,103,832 | 4/1992 | Jackson | 128/675 |
| 5,151,684 | 9/1992 | Johnsen | 340/572 |

OTHER PUBLICATIONS

"Telemetry of Aortic Pressure in Unrestrained Animals", Armentano et al., Medical Progress Through Technology, vol. 16, No. 3, Aug. 1990, Dordrecht (NL), pp. 125–129.

Primary Examiner—Angela D. Sykes
Assistant Examiner—Robert L. Nasser, Jr.
Attorney, Agent, or Firm—Lawrence C. Edelman

[57] ABSTRACT

An electronic labeling and display system for displaying a user defined label created once by the user at a display monitor location and displayed at the remote sensing location and a display monitor.

11 Claims, 2 Drawing Sheets

PROGRAMMABLE ELECTRONIC BLOOD PRESSURE MONITORING LABELS

BACKGROUND OF THE INVENTION

1. Field of the Invention

The present invention relates to Medical Systems and in particular to patient blood pressure monitoring and labeling display systems.

2. Background

It is often necessary in hospitals, health care facilities and other locations to collect and display a variety of medical data of a patient. The medical data is obtained from sensors capable of detecting information on the physical parameters or body condition. Frequently, multiple modes, locations on the patient, and means of obtaining a representative indication of a vital sign of the patient is needed to properly monitor and care for the patient. One such vital sign is blood pressure. A plurality of blood pressures are measured simultaneously at various locations in the blood circulatory system of the patient (e.g. at left atrium, right atrium, left ventricle as well as right ventricle).

One of the considerations in the design or selection of a monitoring system is the speed and facility or ease in connecting and disconnecting the sensors, and fluid tubes to/from the patient as well as electrical support cables and connectors associated with the monitoring apparatus.

As the patient is changed from one level of care to another, it is frequently desirable to increase the level of monitoring to observe additional parameters of vital signs measured at a different location on the body or to change the method of monitoring from invasive to noninvasive or vice versa. This change or increase of monitoring results in the connection and/or reconnection of sensors, support tubes and cables. In addition, during an emergency, the speed at which a patient is treated by a health care provider is affected by the speed at which the patient is functionally connected to those sensors which provide vital signs and other medical input data. Accordingly, whether during emergency or non-emergency conditions, the process of connecting/reconnecting sensors and their associated fluid tubes and electrical cables as well as setting up the associated monitoring apparatus, is both time consuming and can lead the user to mislabeling one or more of the sensors, their associated fluid tubes, and/or at the electronic output display from the sensor.

Furthermore, the user of monitoring systems label the blood pressure sensors manually with either preprinted or hand written identification tags. Such manual labeling is prone to mislabeling of a sensor. In addition, the labels can become separated from the sensor, or become damaged from either handling or from the fluids found in a clinical environment, and thereby become unreadable.

Even if manual labeling of the sensors is not faultily performed, or the labels do not become separated from their associated sensor, a further disadvantage of labeling is that the blood pressure channel associated with each blood pressure sensor has to be labeled by the user twice; once at the sensor, manually as described above; and once again at the remote output display monitor either manually or electronically. The need to label the blood pressure channel twice, either both times manually, or once manually and once electronically at a remote monitoring location from the sensor(s), creates the opportunity for error due to improperly labeling one or more sensors, or by cross-labeling two or more sensors.

It would thus be an advantage to have an electronic display for labeling each pressure sensor of a blood pressure monitor where each label is located physically close to its corresponding pressure sensor.

It would be a further advantage to electronically display a user defined electrical label, created once by the user at a display monitor location and displayed next to or in the visual field of the user of its corresponding pressure sensor, without the user having to re-create the label at the location of the pressure sensor.

SUMMARY OF THE INVENTION

A blood pressure labeling display system for use with a patient monitoring device, which monitoring device includes a plurality of blood pressure transducers coupled to a patient by associated fluid lines, each of said transducers producing electrical signals representing the blood pressure of the patient, and a display device to display the electrical signals from the transducers representing the blood pressure of the patient, the blood pressure labeling display system comprising: (a) a remote connection block in close proximity to the patient for mechanically supporting the blood pressure transducers, comprising, (1) a plurality of blood pressure programmable electronic display labels, each one of the plurality of blood pressure display labels collocated with a corresponding one of the plurality of blood pressure transducers and their associated fluid lines, (2) means for receiving the electrical signals representing the blood pressures of the patient from the transducers, (3) means for transmitting the electrical signals representing the blood pressures of the patient to the display device from the means for receiving electrical signals, (4) means for receiving label data representing a plurality of selections of label content data from a predetermined menu made by the user and for receiving communications/character data for display on each of the plurality of blood pressure programmable electronic display labels; (b) the display device for displaying the electrical signals from the transducers representing the blood pressures of the patient further having a display monitor, the display monitor including, (1) a microprocessor to control the monitor for displaying the electrical signals representing the blood pressures of the patient, (2) means for receiving the transmission of electrical signals representing the blood pressures of the patient from the remote connection block; (c) means for the user to input the plurality of selections of label content data made by the user for display on each of the plurality of blood pressure display labels on the remote connection block; and (d) means for transmitting the plurality of selections of label content made by the user to the programmable electronic display labels on the remote connection block.

DETAILED DESCRIPTION OF THE INVENTION

Figure 1:
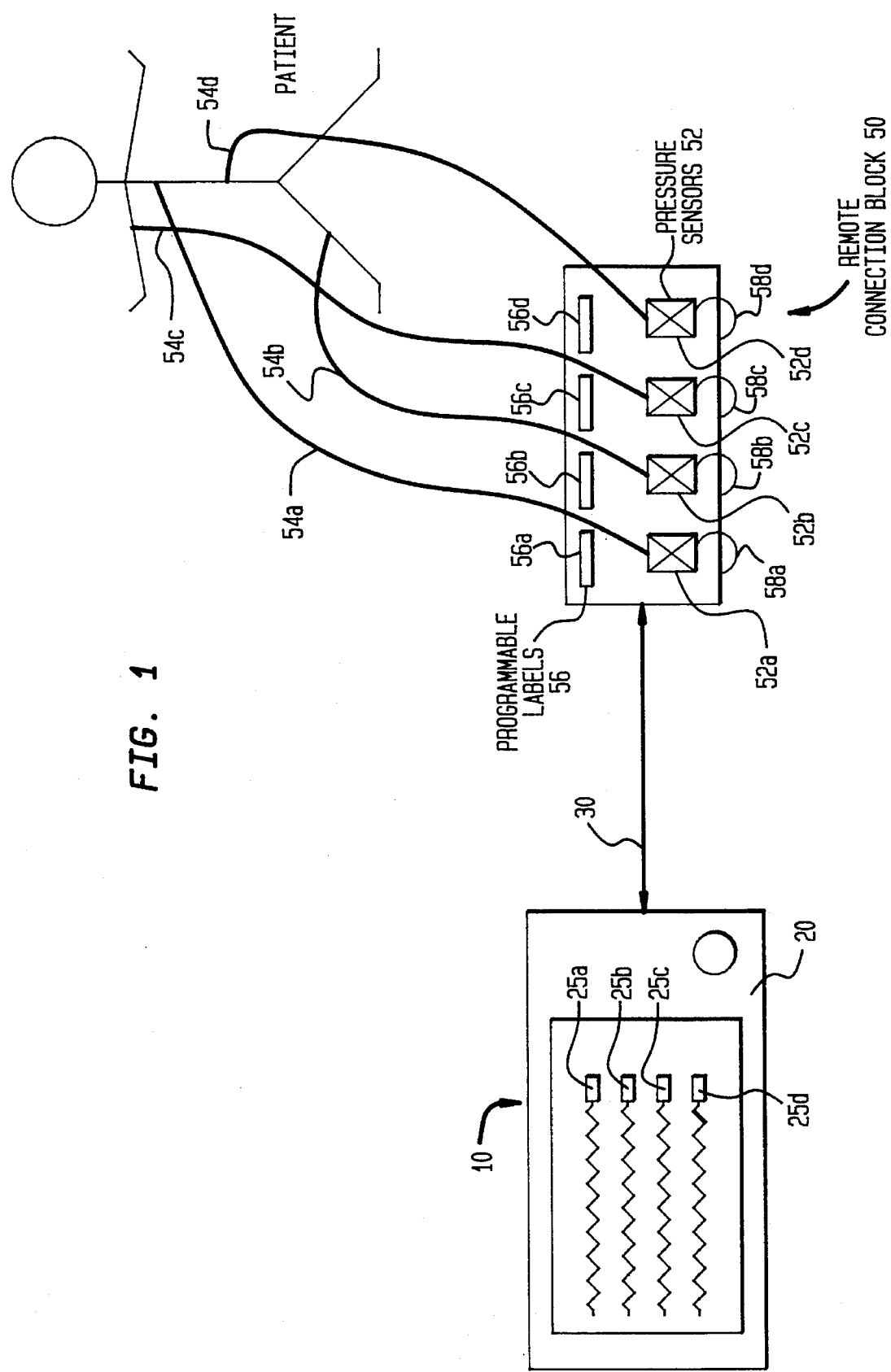
FIG. 1 is a diagram of a programmable electronic blood pressure monitoring label system.
Figure 2:
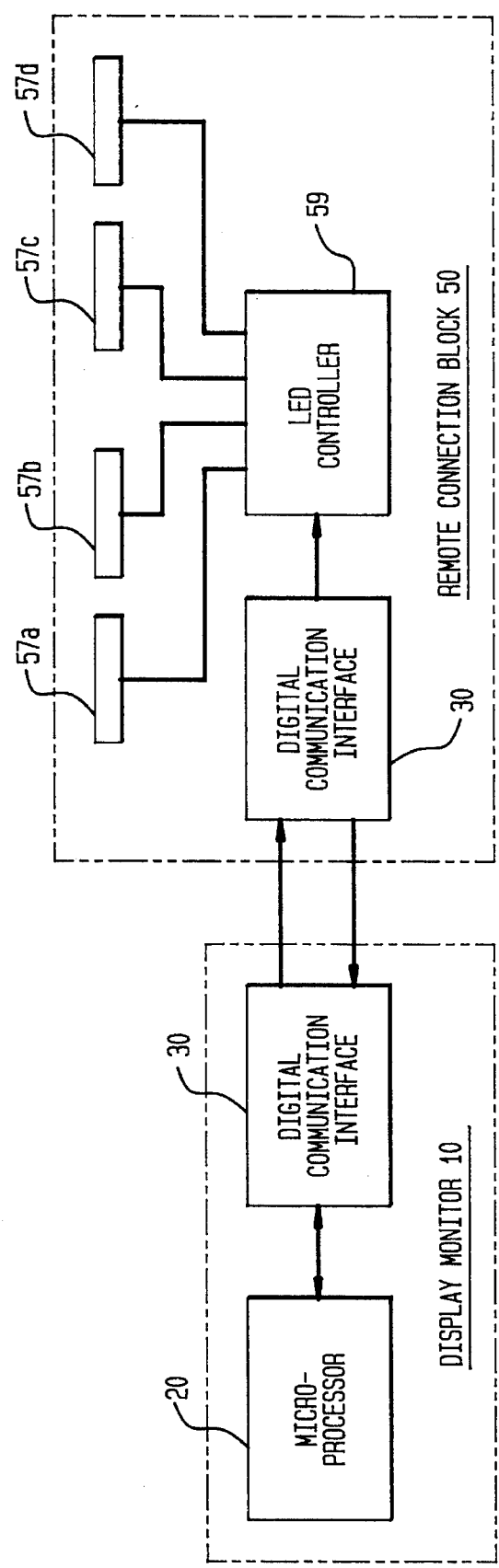
FIG. 2 is a block diagram of the programmable electronic pressure monitoring label system.

The programmable pressure label system comprises a display monitor 10, a digital communications interface link 30, and a remote connection block 50.

Display monitor 10 includes a microprocessor 20 for control of all monitor and display functions as well as for control of the remote connection block 50. Microprocessor 20 is capable of either storing the signal representing patient data received from remote connection block 50 or sending the signal to a screen or other visual indicator.

The remote connection block 50 mechanically supports blood pressure transducers 52 which are connected to fluid lines 54 attached to the patient and supports a blood pressure programmable electronic display label 56 associated with each pressure transducer. Each blood pressure programmable electronic display label 56a, b, c, d is collocated with its pressure transducer 52a, b, c, d which thereby further associates each transducer with its corresponding electronic label. The remote connection block 50 also includes an electrical connection 58a, b, c, d for each pressure transducer.

Control of the remote connection block 50 by the microprocessor 20 and communication between the remote connection block 50 and the display monitor 10 is through the digital communication interface 30. The digital communication interface 30 enables the remote connection block 50 to receive control commands and character data for the programmable labels 56a, b, c, d from the microprocessor 20 inside the display monitor 10. The digital interface 30 also enables the transmission of waveform data as well as instantaneous numerical display digital readout data from the remote connection block to the display monitor for processing and display.

Fluid lines 54 for invasive blood pressure monitoring are each connected at one end to the patient and at the other end to a pressure transducer 52 which produces electrical signals representing the blood pressure of the patient. Electrical cables 58 transmit the electric signals from a respective transducer to the remote connection block 50. Alternatively, the transducers can be of the slide-in module type which slide into a housing in the remote connection block with power and signal coupling being accomplished by mating connectors in the transducer and the remote connection block.

The electrical signals representative of the patient's physiological condition from each pressure transducer 52 are then transmitted via the digital communications link 30 to the microprocessor 20 within the display monitor 10 which can contain the blood pressure signal processing circuitry for display and/or storage. In an alternative embodiment, the remote connection block, rather than the display monitor, can contain the blood pressure signal processing circuitry.

The remote connection block 50 is typically located in close proximity to the patient to facilitate connection of the fluid lines 54 to the patient. Although the display monitor could be located proximate the remote connection block obviating the need for a digital communication link, it is anticipated that the display monitor could be positioned at any location that provides convenient viewing and operation by the care-giver, particularly at a location remote from the remote connection block.

The remote connection block 50 has a plurality of programmable electric display labels which display the selections made and input into the display monitor 10 by the user. The label data for each of the programmable electronic display labels 56a, b, c, d is transmitted to the remote connection block 50 where each of the selections appear on the corresponding programmable label.

In the preferred embodiment of the present invention, the programmable electronic display labels 56a, b, c, d are each made up of a liquid crystal display 57a, b, c, d. Each LCD label can be of any number of alpha-numeric characters made up of several controllable segments. For purposes of illustration and discussion, the LCD labels each have four upper case characters which are each made up of 14 individually controllable segments. The remote connection block 50 also includes an LCD controller 59 which receives command and character data from digital communications interface 30 and which then sends timing signals which enable and disable the character segments of each LCD for display of the label data information by the LCD.

To operate the programmable electronic display labels, the user would go to the location where the display monitor 10 is positioned and select which of the physiological pressures of the patient are to be measured from a predetermined menu displayed on the display monitor, and enters those selections made. In alternative embodiments to the user entering the selections made at the location of the display monitor, the user enters the selections at either the remote connection block, or at a remote location using either wireless remote control or other communications device such as a telephone. After the user confirms the selections made, the label data representing those blood pressure selections is transmitted by the digital communication interface 30 within the display monitor 10 to the remote connection block 50 where each of the selections appear on the programmable electronic display labels. The user would then move to the location where the remote connection block 50 is positioned and insert each of the blood pressure fluid lines 54a, b, c, d into or on the body of the patient at a number of locations in accordance with the blood pressure label data appearing in each of the corresponding programmable electronic display labels 56a, b, c, d. The transducer 52 in each of the fluid lines convert the blood pressure into electrical signals representative of the blood pressure. The signal output from each of the respective transducers is transmitted through electrical connections 58a, b, c, d to an amplifier channel (not shown). These amplifier channels are electrically connected through a multiplexer with an Analog Digital (A/D) converter to convert the sensed and amplified signal(s) which are representative of the blood pressure from a particular location of the patient's body and identified on the programmable label into digital signals (not shown). Digital communication interface 30 is positioned within the remote connection block 50 and transmits these digital signals to the display monitor 10. Although the preferred embodiment of the present invention multiplexes the signals from each of the transducers 52 and transmits them serially to the digital communication interface 30 within the display monitor 10, it is understood by those skilled in the art that virtually any means of transmission of the signals from the remote connection block 50 to the display monitor 10 can be utilized, including a direct conductor set for transmitting, without multiplexing, the signals generated from each transducer along a separate conductor from the remote connection block to the display monitor.

The digital communication interface 30 within the display monitor 10 receives the signals from the remote connection block 50 where they are converted to numerical blood pressure readout and/or a blood pressure waveform for display.

In an alternative embodiment, the label data representing the blood pressure selections made by the user at the monitor is transmitted not only to programmable electronic display labels 56a, 56b, 56c, 56d in the remote connection block, but also to corresponding programmed electronic display labels 25a, 25b, 25c, 25d for display on monitor 10 together with the associated blood pressure data. Thus, the same programmed electronic display label appears in the programmable electronic display labels 56*a, b, c, d* next to the corresponding pressure transducer 52*a, b, c, d* from which the signals originate. In this alternative embodiment, the user creates the label once electronically which is displayed both on the monitor as well as collocated with its associated sensor.

By electronic labeling and displaying a user defined electrical label, created once by the user at a display monitor location and displayed either at the remote sensing location, or at both the remote sensing location as well as at the display monitor, the blood pressure data, the associated corresponding programmed labels, and associated corresponding pressure sensor fluid lines are correctly matched to one another at both the display monitor as well as at the remote connection block.

While the present invention has been particularly shown and described with reference to preferred embodiments thereof, it will be understood by those skilled in the art that various changes in form and details may be made therein without departing form the spirit and scope of the invention.

We claim:

1. In combination:
   a patient monitoring device, which monitoring device is adapted for use with a plurality of blood pressure transducers adapted for coupling to a patient by associated fluid lines, each of said transducers producing electrical signals representing a different blood pressure of the patient, and which monitoring device includes, a display device for displaying the electrical signals from the transducers representing the different blood pressures of the patient, said display device having a display monitor including, (1) a microprocessor to control the display monitor for displaying the electrical signals representing the blood pressures of the patient, and (2) means for receiving the transmission of electrical signals representing the blood pressures of the patient from a remote connection block; and
   a blood pressure labeling display system comprising,
   (a) a remote connection block in close proximity to the patient for mechanically supporting the blood pressure transducers, comprising;
      (1) a plurality of blood pressure programmable electronic display labels, each one of the plurality of blood pressure display labels adapted to be collocated with a corresponding one of the plurality of blood pressure transducers and their associated fluid lines;
      (2) means for receiving the electrical signals representing the blood pressures of the patient from the transducers;
      (3) means for transmitting the electrical signals representing the blood pressures of the patient to the display device from the means for receiving electrical signals; and
      (4) means for receiving label data representing a plurality of selections of label content data from a predetermined menu made by a user and for receiving communications/character data for display on each of the plurality of blood pressure programmable electronic display labels;
   (b) means for the user to input the plurality of selections of label content data made by the user for display on each of the plurality of blood pressure display labels on the remote connection block; and
   (c) means for transmitting the plurality of selections of label content data made by the user to the programmable electronic display labels on the remote connection block.

2. The combination of claim 1 wherein the display monitor further includes a plurality of display monitor display labels and wherein the plurality of selections of label content made by the user for display on each of the blood pressure display labels is transmitted to the plurality of display monitor display labels.

3. The combination of claim 1 wherein the means for the user to input the plurality of selections of label content data is located on the display monitor.

4. The combination of claim 3 wherein the means for the user to input the plurality of selections further includes means for receiving input commands from a wireless remote control.

5. The combination of claim 3 wherein the plurality of blood pressure programmable electronic display labels are liquid crystal displays, and further including a liquid crystal display controller for receiving command and character data from the display monitor and for sending timing signals which enable/disable each liquid crystal display.

6. The combination of claim 5 wherein the liquid crystal display controller is in the remote connection block.

7. The combination of claim 1 where the means for the user to input the plurality of selections of label content data is located on the remote connection block.

8. The combination of claim 1 wherein the display monitor further includes blood pressure signal processing circuitry for displaying the electrical signals from the remote connection block on the display monitor.

9. The combination of claim 1 wherein the remote connection block further includes blood pressure signal processing circuitry for storage of the electrical signals in the remote connection block.

10. The combination of claim 1 wherein the electrical signal output received from each transducer is transmitted through a respective amplifier channel which amplifies the electrical signal output and transmits said amplified output to a multiplexer with an analog/digital converter to multiplex the amplified outputs and analog/digital convert the amplified and multiplexed output and to serially transmit said amplified, converted and multiplexed output to the display monitor.

11. The combination of claim 1 wherein the means for transmission of the electrical signals representing the blood pressures of the patient to the display monitor includes a plurality of conductors for transmitting the electrical signals from each one of the plurality of blood pressure transducers along a corresponding one of the plurality of conductors from the remote connection block to the display monitor.

\* \* \* \* \*